US007060290B1

(12) United States Patent
Morimoto et al.

(10) Patent No.: US 7,060,290 B1
(45) Date of Patent: Jun. 13, 2006

(54) PHOSPHOCHOLINE LINKED PRODRUG DERIVATIVES

(75) Inventors: Bruce H. Morimoto, Redwood City, CA (US); Peter L. Barker, Pleasanton, CA (US)

(73) Assignee: Supergen, Inc., Dublin, CA (US)

( * ) Notice: Subject to any disclaimer, the term of this patent is extended or adjusted under 35 U.S.C. 154(b) by 0 days.

(21) Appl. No.: 09/890,006

(22) PCT Filed: Feb. 16, 2000

(86) PCT No.: PCT/US00/04140

§ 371 (c)(1),
(2), (4) Date: Oct. 25, 2001

(87) PCT Pub. No.: WO00/48572

PCT Pub. Date: Aug. 24, 2000

Related U.S. Application Data

(60) Provisional application No. 60/120,483, filed on Feb. 18, 1999.

(51) Int. Cl.
    *A61K 9/127*   (2006.01)
    *A61K 31/665*  (2006.01)
    *A61K 31/675*  (2006.01)
    *A61K 31/685*  (2006.01)
    *C07D 259/00*  (2006.01)
    *C07D 487/22*  (2006.01)
    *C07F 9/02*    (2006.01)

(52) U.S. Cl. ............... 424/450; 514/78; 514/79; 514/100; 540/456; 540/460; 540/478; 544/243; 544/337; 546/23; 548/113; 548/119

(58) Field of Classification Search ............... 424/450; 514/78–79, 458, 573, 553, 557, 725, 100; 428/402.2, 169; 554/79; 540/456, 460, 540/478; 544/243, 337; 546/23; 548/113, 548/119

See application file for complete search history.

(56) References Cited

U.S. PATENT DOCUMENTS 5,534,499 A * 7/1996 Ansell .................. 514/25
5,703,063 A * 12/1997 Chasalow
5,776,915 A * 7/1998 Peterson
5,830,432 A   11/1998 Chasalow

FOREIGN PATENT DOCUMENTS

WO        96/16680    6/1996
WO    WO 98/11906    3/1998

* cited by examiner

Primary Examiner—Gollamudi S. Kishore
(74) Attorney, Agent, or Firm—Darby & Darby

(57) ABSTRACT

Disclosed are compounds of general formula (I) that function as prodrugs, thereby increasing bioavailabilies of the linked therapeutic agents, wherein the LINKER is (i) substituted or unsubstituted alkyl, (ii) substituted or unsubstituted alkenyl, (iii) substituted or unsubstituted alkanoyl, (iv) substituted or unsubstituted alkenoyl wherein the double bond is cis, and (v) (ortho or para) carbonyl-substituted aryl; and wherein the subtituent is each an independent group or linked together thereby forming a ring; and wherein X is one or more substituted or unsubstituted group containing one or more O, N, or S atom and wherein the substituent is each an independent group or linked together thereby forming a ring; and wherein the therapeutic agent is an alcohol-containing water-insoluble steroids or another alcohol containing compounds and methods to prepare such compounds.

12 Claims, No Drawings

PHOSPHOCHOLINE LINKED PRODRUG DERIVATIVES

CROSS-REFERENCE TO RELATED APPLICATION

This application is a 371 of International Application No. PCT/US00/04140, filed Feb. 16, 2000, which claims priority of U.S. Provisional Patent Application No. 60/120,483, filed Feb. 18, 1999, the entire disclosure of which is incorporated by reference herein.

FIELD OF THE INVENTION

This invention pertains to methods and compositions for increasing the aqueous solubility and bio-availability of bioactive agents by conjugating them to phospholipids.

BACKGROUND OF THE INVENTION

Conventional means for delivering pharmaceutical and therapeutic agents to mammals often are severely limited by chemical and physical barriers to uptake, as well as by susceptibility of administered agents to rapid metabolic inactivation following uptake. Oral delivery of many biologically-active agents would be the route of choice if not for the extreme pH of the stomach, the action of proteolytic and other digestive enzymes in the intestine, and the impermeability of gastrointestinal membranes to the active ingredient.

Methods for orally administering vulnerable pharmacological agents have relied on co-administration of adjuvants (e.g. resorcinols and non-ionic surfactants such as polyoxyethylene oleyl ether and n-hexadecyl polyethylene ether) to artificially increase the permeability of the intestinal walls; co-administration of enzymatic inhibitors (e.g. pancreatic trypsin inhibitor, diisopropylfluorophosphate (DFP) and trasylol) to avoid enzymatic degradation; and encapsulation of the active agent in liposomes or other delivery vehicles.

Irrespective of the mode of administration of many therapeutic compounds, once they gain access to body tissues or fluids they are then subject to rapid inactivation in the liver, termed the first-pass effect. Orally administered compounds in particular are rapidly delivered to the liver via the portal circulation. Many compounds are acted upon by mixed-function oxidases, Phase I enzymes and other liver enzymes to produce inactive glucuronides, hippurates, glycyl and acetyl derivatives, which are rapidly excreted by the kidney.

There is thus a need in the art for methods and compositions to enable potential therapeutic agents to be rapidly absorbed in the intestine and avoid first-pass inactivation in the liver.

SUMMARY OF THE INVENTION

It has now been unexpectedly discovered that conjugation of many biologically active agents to phospholipid via a phosphodiester bond will significantly enhance the bioactivity and/or the bioavailability of such agents.

In one aspect, the present invention provides a method for increasing the bioavailability of a pharmaceutical agent, comprising the steps of conjugating said agent to one or more phospholipid moieties, recovering said biologically active agent conjugated to said phosphocholine and administering said agent to a mammal wherein said agent in conjugated form is significantly more soluble in aqueous media than said agent in unconjugated form.

In yet another aspect, the present invention provides a composition of matter comprising an isolated phospholipid derivative of salicylic acid.

In yet another aspect, the present invention provides a pharmaceutical formulation for treating a mammal suffering from osteoporosis comprising an isolated phospholipid derivative of a compound selected from the group consisting of estrone or estradiol and a pharmaceutically acceptable carrier or diluents.

In yet another aspect, the present invention provides a composition of matter comprising an isolated phospholipid derivative of an antibiotic selected from the group consisting of cephalosporin P1, fusidic acid and helvolic acid.

In yet another aspect, the present invention provides a composition of matter comprising an isolated phospholipid derivative of dehydroepiandosterone.

These and other aspects of the present invention will be apparent to those of ordinary skill in the art in light of the present description, claims and drawings.

DETAILED DESCRIPTION OF THE INVENTION

All patent applications, patents, and literature references cited in this specification are hereby incorporated by reference in their entirety. In case of inconsistencies, the present description, including definitions, will prevail.

Definitions

"Phospholipid-conjugated" or "phospholipid-derivatized" defined herein as covalently bonded to a phospholipid moiety via a phosphodiester linkage.

"Significantly enhanced bioactivity" or "significantly more soluble in aqueous media" in terms of the conjugated drugs of the present invention is defined herein as no less than 5 to 10-fold increased biological activity and/or aqueous solubility as compared to the unconjugated parent compound when administered by the same route.

The present invention is directed to increasing the bioavailability and/or aqueous solubility of pharmaceutically active agents, specifically by conjugation of such agents to phospholipids, such as a phosphocholine moiety via a phosphodiester bond.

In accordance with the present invention, therapeutic substances will benefit by increasing their water solubility (and their bioavailability) by forming a phosphodiester between an (a) alcohol, and (b) a phospholipid. Non-limiting examples of the phospholipid include phosphocholine, phosphoserine, phosphotyrosine, phosphoethanolamine, n-monoakyl-phosphoethanolamine and N, N-dialkyl-phosphoethanolamine (all commercially available from Aldrich Chemical, Milwaukee, Wis.). Phosphocholine is particularly preferred as the phospholipid.

Phosphocholine is a ubiquitous component of biological membranes, usually present in the form of phosphatidyl choline, i.e., attached via a phosphodiester bond to diacyl glycerol. The two most common phosphocholine-containing molecules are lecithin and sphingomyelin. Both of these compounds can be hydrolyzed by phospholipase C at the phosphocholine phosphodiester bond to release diacyl glycerol and ceramides, respectively. Importantly, both lecithin and sphingomyelin, which are present in food, are absorbed in the gastrointestinal tract, incorporated into HDL- and LDL-cholesterol, and transported through the blood without significant first-pass metabolism in the liver.

In accordance with the present invention, conjugation of one or more phospholipid moieties to lipophilic compounds will render them more hydrophilic, without abrogating their ability to traverse biological membranes. Without wishing to be bound by theory, it is contemplated that phospholipid conjugation will, in most cases, mask the biological activity of the conjugated compounds. The phospholipid conjugates will persist in conjugated form until they encounter enzymes such as phospholipase C, sphingomyelinase and non-specific esterases, which are members of the signal transduction pathway (*Methods in Enzymotofy*, Vol. 197, E. Dennis, editor, Academic Press, NY) and are present in the circulation and on target tissues. These enzymes will then remove the phospholipid moiety and liberate the original compound with its biological activity intact. The above-mentioned enzymes are specific for phosphocholine; other esterases of the signal transduction system would hydrolyze the other phosphoesters (*Methods in Enzymology*, Vol. 201, T. Hunter, Academic Press, NY, Beth Sefton, editor). In this manner, addition of phospholipid is expected to protect compounds from first-pass inactivation in the liver and allow them to reach their sites of action in the blood or in peripheral tissues.

Pharmaceutical agents suitable for use in the present invention include, without limitation, lipophilic compounds that exhibit poor solubility in biological fluids, as well as compounds that are rapidly metabolized in the liver to hippurate, glucuronate, or other derivatives. Non-limiting examples of suitable compounds include those that are not presently utilized in pharmaceutical applications, in particular as orally administrable agents, because of problems with solubility, uptake, and/or metabolism. The only requirements for an agent to be used in the present invention are 1) the presence of a free alcohol functional group to which a phospholipid may be attached, and 2) the susceptibility of the resulting phosphodiester bond to cleavage by phospholipase C, sphingomyelinase or other mammalian esterases.

Examples of pharmaceutical agents suitable for use in the present invention include without limitation steroids, catecholamines such as epinephrine or norepinephrine, prostaglandins such as prostaglandin E1 or E2, leukotrienes such as leukotriene B4, C4 or D4 and peptides. Peptides for use in the present invention are those which contain serine or threonine and preferably should not be longer than 10–15 amino acid residues in length such as Leutinizing Hormone Releasing Hormone (LHRH) (a 10 amino acid peptide) and its analogues. Preferred starting compounds or pharmacological agents include testosterone (available from Sigma, St. Louis, Mo.), etiocholanolone (Sigma), estradiol (Sigma), estrone (Sigma) and dehydroepiandrosterone (Sigma). These steroids have only limited activity when administered orally.

In an alternative embodiment of the present invention antibiotics, such as cephalosporin P1, can be conjugated to phospholipids in order to increase its aqueous solubility and decrease it metabolism on the first pass through the liver and excretion on the first pass through the kidney. Non-limiting examples of compounds for use in this embodiment of the present invention include cephalosporin P1 (isolated as described in Burton et al., *Biochem. J.* 50:168–174, 1951; Halsall et al., *Chem. Comm.*, pp. 685–687, 1966), fusidic acid (commercially available from Sigma), and helvolic acid (commercially available from Sigma). Use of these antibiotics has been limited because of an inability to development therapeutic serum and tissue levels in recipient mammals and, perhaps, because of the ease of development of resistance. The apparent resistance may be caused by induction of metabolic enzymes as occurs with other steroidal therapeutic agents.

Non-limiting examples of additional substances for use in the present invention containing a free alcohol group include the steroidal substances mentioned above (DHEA, etcholanolone, testosterone, estradiol, estrone, catecholamines, etc.), the antibiotics mentioned above, aglycones including cardiac glycosides, such as digoxigenin (commercially available from Sigma), digitoxigenin (commercially available from Sigma), ouabagenin (commercially available from Sigma) and salicylic acid (commercially available from Sigma).

Presented below is a further list of non-limiting examples of compounds for use in the present invention. Following the name of the compound, presented in parentheses is the number assigned to the compound in the Merck Index, 1996, 12th Edition. Menadiol (5873), Metronidazole (6242), Clindamycin (2414), Pentaerythritol Tetranitrate (7249), Mesalamine (5964), β-Tocopherol (9632), γ-Tocopherol (9633), δ-Tocopherol (9634), Roxindole (8432), Vitamin E (10159), Styramate (9027), Strophanthidin (9015), Vitamin A (10150), Vitamin $D_2$ (10156), Vitamin $D_3$ (10157), Vitamin $A_2$ (10151), Calcitriol (1681), Diflunisal (3190), Clavulanic Acid (2402), Retinoic Acid (8333), Mazindole (5801).

A compound particularly well-suited for use in the present invention is the cyclic Urea-based HIV-1 protease inhibitor DMP-323 (*J. Med. Chem.* 39:2156–2169, 1996). Due to its low aqueous solubility investigators found that there was variability in the compounds bioavailability upon administration to patients and inconsistent efficacy. Addition of a phospholipid moiety is expected to improve its therapeutic use.

Other compounds well-suited for use in the present invention include aglycones from cardiac glycosides such as digoxigenin, digitoxigenin and ouabagenin (all commercially available from Sigma, St. Louis, Mo.).

In addition to increasing the solubility of the above-identified compounds, the primary effect of conjugation to a phospholipid moiety to the following water soluble compounds is expected to be an increased half-life, that is to say, they will be long-acting forms of the parent compounds. Non-limiting examples of such compounds include Isoproterenol (5236), Propranolol (8025), Methyldopa (6132), Epinephrine (3656), Codine (2525), Codine Phosphate (2528), Acetaminophen (45), Aspirin (886).

The conjugated therapeutic agents will be at least ten times more water soluble then the original alcohol. This will increase their bioavailability and decrease their metabolism to, e.g., the 3-glycoside in the case of steroids, which should be a major excretion pathway. The decreased glycoside formation will be caused by the presence of the phosphoester at that site. The derivative is not expected to be active prior to hydrolysis of the phospholipid group. The present inventor has found that lymphocytes have an enzyme on their cell membrane that cleaves phosphocholine from other compounds (for example, sphingomyelin or lecithin) to release phosphocholine and the other ester conjugate (ceramide or diacylglycerol). The activity of this enzyme is stimulated ten-fold by TGF-α (data not shown). Without wishing to be bound by theory, it is believed that use of phospholipid-conjugated antibiotics of the present invention will lead to high concentrations of active agents at the site of an infection by the following mechanism. Lymphocytes are attracted to the site of an infection or inflammation where they release TGF-α, which, in turn, stimulates phospholipid hydrolysis in other subtypes. This same process will lead to local release of an active form of the antibiotic from the phospholipid diester conjugate. Because of the response of the enzyme to local concentrations of TGF-α, there should be a correspondingly high local concentration of the antibiotic. This will lead to effective therapy and lower toxicity.

According to the present invention, starting compounds may be converted to phospholipid derivatives using any methods that are known in the art. In one preferred embodiment, phosphocholine (obtainable from Sigma Chemicals, St. Louis, Mo.) is reacted with a soluble carbodiimide, preferably 1-ethyl-3(3-dimethyl-aminopropyl)carbodiimide hydrochloride (EDAC, Sigma) in an active ester condensation reaction. This carbodiimide is preferred because it, similar to phosphocholine, is water-soluble. The active phosphoester intermediate is then reacted with a pharmaceutically active agent to yield the desired phosphocholine ester. The reaction is shown in Example 1 below. Phosphocholine in water is reacted with EDAC to yield the active ester. This is then reacted with, e.g., testosterone or other biologically active starting compounds etc., to yield the final product

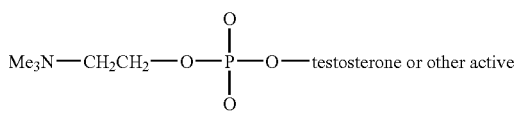

or other active esterification product. The product is expected to be essentially water-soluble and thus easily separated from the starting compound by conventional extraction and/or separation methods e.g. Flash Chromatography, Thin Layer Chromatography, High Performance Liquid Chromatography (HPLC) and the like, as is known to those of ordinary skill in the art.

Alternate methods for synthesis of phosphocholine derivatives include phosphorylation of the steroid, peptide, etc. with DPPP to give a phosphate ester, e.g., testosterone phosphate, which is coupled to choline using EDAC as the complexing agent.

Alternately, the alcohol ("drug") may be reacted with phosphorous oxychloride and the aminoalcohol component added in excess. In this way all of the unreacted phosphorous oxychloride will be used up. The phosphochloride ester intermediate can also be isolated and reacted as a second step with the amino-alcohol component (choline, etc.). The final products can be purified by HPLC.

The phospholipid derivatized drugs of the present invention are expected to demonstrate enhanced biological activities, increased bioavailability and increased aqueous solubility. For example, etiocholanolone is metabolized by formation of the glucuronide in the liver of a mammal. After oral administration, about 99% of all free etiocholanolone is inactivated on each pass through the liver. When etiocholanolone is orally administered, it is absorbed in the gastrointestinal tract and transported via the portal circulation directly to the liver. Subsequently, only a fraction of a percent of the administered drug is biologically available for function. In contrast, phosphocholine-conjugated etiocholanolone may bind to form Low Density Lipoprotein (LDL) and High Density Lipoprotein (HDL) cholesterol and is not expected to be degraded on first passage through the liver. In its phosphocholine-derivatized form, it is believed that about 80% of the etiocholanolone would not be metabolized at each pass. When the phosphocholine moiety is removed by an esterase, such as phospholipase C, sphingomyelinase, etc., then the parent compound will be available for binding and function in the target tissue. Glucuronidation would only occur on its return to the liver after removal of the phosphocholine moiety.

The phospholipid-conjugated compounds of the present invention may be administered therapeutically by any route known in the art, e.g., orally, intravenously, intramuscularly, subcutaneously, by inhalation or in aerosol form, and topically. The present invention is particularly applicable to compounds that, in their unconjugated state, cannot be effectively administered by the oral route.

The phospholipid-conjugated compounds of the present invention can be tested for efficacy as follows. A starting compound, and its phospholipid derivative, may be administered by any of the above routes to a test animal, e.g., rat, mouse, rabbit, guinea pig, and the like. Serum samples are then collected at increasing times after administration, and the levels of the starting and conjugated compound are assayed and compared. It will be understood by those skilled in the art that the method of assay will depend upon the starting compound. In the case of steroids or peptides, High-Performance Liquid Chromatography, Thin-Layer Chromatography, or immunoassay may be used to quantify serum levels. When the starting compounds are gonadal steroids, it may also be necessary to gonadectomize the test animals prior to drug administration, so as to suppress endogenous production of the test compound. Successful compounds are those whose serum level is increased significantly by administration of the phospholipid derivative relative to administration of the starting compound or by their ability to reach therapeutically significant serum levels when administered by an alternate route, e.g. orally.

In a second phase, the starting compound and its phospholipid derivative will be administered to test animals, and the physiological effect of the compounds assayed over time. For example, for etiocholanolone and its phospholipid derivative(s), rate of weight gain and changes in basal metabolic rate are measured. Estradiol, estrone and their phosphocholine derivatives will be administered by gavage to ovariectomized mice or rats and changes in uterine weight, breast development and estradiol blood levels will be measured. Testosterone and its phosphocholine derivative will be administered orally to castrate mice or rats and changes in seminal vesicles, prostate size, and levator and muscle will be determined. Theophylline and its phosphocholine derivatives will be given orally to rats and the blood levels over the next 6 hours will be determined. From these tests, the degree to which the phospholipid derivatives are more potent than the underivatized parent compound will be determined, i.e., the same response will be achieved with a smaller dose of the derivatized compound than the parent compound. This will be a measure of greater potency. Successful compounds are those whose functional endpoints are significantly lower for phospholipid derivatives than for the starting compounds.

In a preferred embodiment of the present invention, testosterone is converted to testosterone-17-phosphocholine, estrone is converted to estrone-3-phosphocholine and estradiol is converted to estradiol-3-phosphocholine or estradiol-17-phosphocholine. In like manner, theophylline is converted to theophylline phosphocholine. These compounds will frequently be given as replacement therapy for various hormone deficiencies and as pharmacological therapies in other cases. Theophylline is given to treat asthma, estradiol is administered to treat osteoporosis, etiocholanolone is given as a haemapoetic agent, to promote weight loss and to reduce diabetic blood sugar levels. Similar derivatives could also be used to provide enhanced levels of epinephrine.

The present invention also provides pharmaceutical formulations and dosage forms comprising the phospholipid-derivatized drugs of the present invention. The pharmaceutical formulations of the present invention may also include, as optional ingredients, pharmaceutically acceptable vehicles, carriers, diluents, solubilizing or emulsifying agents, and salts of the type well known to those of ordinary skill in the art.

The phospholipid-derivatized drugs of the present invention can be incorporated into pharmaceutical formulations to be used to treat mammals. Pharmaceutical formulations comprising the phospholipid-conjugated drugs of the present invention as at least one of the active ingredients, would in addition optionally comprise pharmaceutically-acceptable carriers, diluents, fillers, salts and other materials well-known in the art depending upon the dosage form utilized. For example, preferred parenteral dosage forms may comprise a sterile isotonic saline solution, 0.5 N sodium chloride, 5% dextrose and the like. Methyl cellulose or carboxymethyl cellulose may be employed in oral dosage forms as suspending agents in buffered saline or in cyclodextran solutions to enhance solubility.

It will be appreciated that the unit content of active ingredient or ingredients contained in an individual dose or dosage form need not in itself constitute an effective amount for the various usages of the phospholipid-derivatized drugs of the present invention since the necessary effective amount can be reached by administration of a plurality of such dosage forms.

The following examples are intended to further illustrate the present invention without limiting it thereof.

EXAMPLE 1

Synthesis of Phosphocholine Derivatives

Method 1

Phosphocholine (Sigma) (0.1 mol) is stirred in pyridine (Fisher, VWR) (100 ml) with 0.1 mol of morpholine (Sigma) and 0.1 mol of DDC (Sigma) for 6 hours under nitrogen or argon. At this point the reaction complex is stirred while 0.1 mol of steroid (etiocholanolone, estradiol, testosterone) are added. After stirring for an additional 3 hours the reaction mixture is diluted with 1 liter of ice water. The insoluble N,N' dicyclohexylurea is removed by filtration and the aqueous fraction is extracted with 4×0.5 volumes of ethyl acetate. The ethyl acetate is washed with saturated brine (0.1 vol) to remove the pyridine and dried over sodium sulfate. The solvent is removed by filtration and the product isolated by LH-20 column chromatography or by preparative HPLC.

Method 2

Phosphocholine (0.1 mol), steroid (0.1 mol) as above and DCC (0.12 mol) are stirred in 100 ml of pyridine (VWR) at 80° for 6 hours under nitrogen. The solution is diluted with 600 ml of water and processed as described above.

Method 3

Testosterone or other steroid, prostaglandin, etc. (0.1 mol) is reacted with $POCl_3$ in pyridine to yield the steroid phosphate. This product after drying in pyridine will then be reacted with 0.1 mol of EDAC at a rate just sufficient to maintain the pH at 7.0. The product is then purified as described above.

The compounds will then be analyzed by HPLC to determine purity of the reaction product, by NMR to verify the structure and by UV and IR spectra to determine their identity. Treatment with a phosphodiesterase will then be used to cleave the diester to further establish the structural identity.

EXAMPLE 2

Pharmacokinetics of Testosterone and its Phosphocholine Derivative

The phosphocholine derivatives of testosterone (about 5 mg) is dissolved in 20 ml of buffered saline or in 20 ml of 40% cyclodextran in saline and given orally to human volunteers. Alternatively, testosterone (5 mg) is suspended in a carboxymethyl cellulose suspending media, vortexed and then given orally. Blood samples will be taken at 30, 60, 120, 240, 360 and 720 minutes post-administration and collected in green top tubes. The blood samples are centrifuged and the plasma collected and stored as aliquots in microfuge tubes. The samples are then analyzed for testosterone in duplicate using a standard RIA kit (Diagnostics Products Corp., Tarzana, Calif.).

EXAMPLE 3

Measurement of Bioactivity of Phosphocholine Derivatives

The bioactivity of orally administered estradiol and estradiol phosphocholine will be determined in ovariectomized mice or rats. In addition, other animals will be briefly anesthetized and the steroid phosphocholine derivative or the free steroid will be administered intraperitoneally (IP). After 2 days the animals are sacrificed and the 4th and 9th inguinal breast tissue will be isolated. At the same time the uteri will be isolated and weighed. It is expected that the phosphocholine derivatized steroid will be more active than the parent compound when administered orally and by IP injection.

Estradiol and its phosphocholine derivative will also be administered by gavage to ovariectomized mice or rats and changes in uterine weight, breast development and estradiol blood levels will be measured. Estradiol will be measured with an RIA kit from Diagnostics Products Corp. (Tarzana, Calif.).

Testosterone and its phosphocholine derivative will be administered orally to castrate male mice or rats and changes in seminal vesicles, prostate size, and levator ani muscle will be determined. Testosterone blood levels will also be measured by RIA using a kit from Diagnostics Products Corp. (Tarzana, Calif.). The compounds will also be characterized by UKV. Responses will also be measured after IP injection.

Theophylline and its phosphocholine derivatives will be given orally to rats and the blood levels of theophylline will be measured over the next 6 hours using an RIA kit (Diagnostics Products Corp., Tarzana, Calif.).

From these tests, the degree to which the phosphocholine derivatives are more potent than the underivatized parent hormone can be determined; i.e., the same response will be achieved with a smaller dose of the derivatized compound than the 25 parent compound. This will be a measure of greater potency.

EXAMPLE 4

Synthesis of Dehydroepiandrosterone (DHEA)-Phosphocholine Derivative

A dehydroepiandrosterone(DHEA)-phosphocholine derivative was synthesized as follows: 1 mg of phosphocholine (calcium salt; Sigma Chemical, St. Louis, Mo.) was dissolved in 0.5 ml of formamide (Cat # S-7503; Lot # 55HO257; Sigma Chemical) and 0.5 ml of pyridine (Cat # P-4036; Lot # 55H1489; Sigma Chemical). 0.025 mCi of (1,2,6,7 $^3$H(n)-Dehydroepiandrosterone (Cat # NET814; Lot # 3146097; 89.2 Ci/mmol; Dupont, NEN Products, Boston, Mass.) in 0.025 ml of ethanol was added. The reaction was catalyzed by the addition (as the dry solid) of 5 mg of dicyclohexylcarbodiimide (Cat # D-3129; Lot # 34hO647; Sigma Chemical). The reaction mixture was incubated overnight at room temperature. In the morning, 9 ml of water was added and the mixture extracted 3 times with 10 ml portions of benzene. The benzene extracts were combined and aliquots of both phases were counted in a scintillation counter. The results are set forth below:

Aqueous Phase 10,729 cpm (0.01 ml)
Benzene Phase 1,121 cpm (0.01 ml)

The aqueous layer was re-extracted with benzene. The second benzene extraction yielded 272 cpm (0.01 M1) as a confirmation.

Free DHEA starting material would have been extracted quantitatively into benzene with this protocol. The observation that the reaction product remains in the aqueous phase confirms its increased hydrophilic characteristics.

EXAMPLE 5

DHEA-3-Phosphocholine; Synthesis and Bioactivity

DHEA-phosphocholine (DHEA-PC) was synthesized by sequential reaction of DHEA, choline, and water with phosphorous oxychloride. The synthetic product had the same HPLC retention time and the same mass-spectrum as did the endogenous, actual compound. It was hydrolyzed by neutral sphingomylenase, but not by acidic sphingomylenase. When human serum extracts were analyzed, mass fragments were detected at the same retention time as synthetic material. When DHEA-PC was administered to mice, it potentiated dinitrochlorobenzene-induced sensitization as detailed below.

EXAMPLE 6

DHEA-PC Potentiates DNCB-Induced Immunological Sensitization

The effects of DHEA-PC on cutaneous contact hypersensitivity was studied. In this study, mice (Balb/c) were immunologically challenged with DNCB (2% in ethanol) applied to a 2 cm area on the back. The steroid was injected subcutaneously (100 μg/day/mouse) throughout the twelve-day study period. Ears were rechallenged with DNCB (1% in ethanol) on days 7–12 and swelling was measured daily in order to evaluate the effect on the immune system.

During days 7–12, DHEA-PC enhanced the cutaneous hypersensitivity immune response similar to native steroids (DHEA and DHEA-sulfate). The response to these three hormones was not suppressed by dexamethasone even though, when administered by itself, dexamethasone suppressed the immune response below the control. This shows that all three hormones induced a similar, high level response.

EXAMPLE 7

Novel Phosphocholine Synthetic Method

DHEA (I) (82.0 g, 0.284 mol, Steraloids, Inc., Wilton, N.H.) was dissolved in a 5 L, 3 necked, round bottom flask in dry benzene (1.5 L, Fisher, Pittsburgh, Pa.). Gentle heating was applied to facilitate the process. Triethylamine (30.3 g, 41.6 mL, 0.30 mol, Aldrich, Milwaukee, Wis.) was added all at once. After the reaction was cooled down to room temperature, oxyphosphorus trichloride (43.6 g, 26 mL, 0.284 mol, Fluka, Ronkonkoma, N.Y.) was added in one portion. The mixture was stirred under nitrogen overnight (12 hours). The precipitate was filtered off via canula transfer under nitrogen, and washed once with dry benzene (300 mL). To the combined clear benzene solution was added ethylene glycol (18.6 g, 0.30 mol, Aldrich) and triethylamine (61 g, 0.60 mol, Aldrich). The mixture was stirred rapidly for 16 hours at room temperature. Thin layer

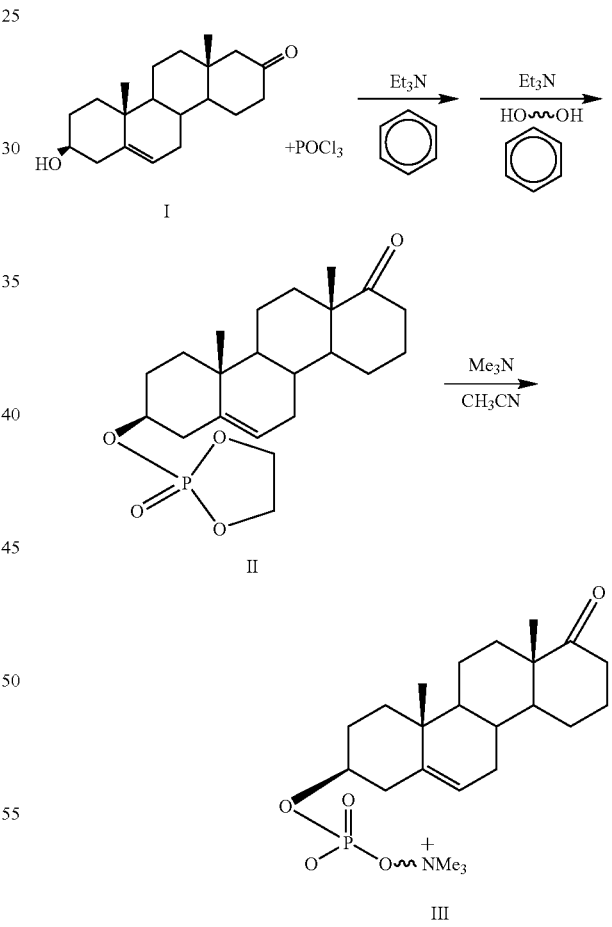

chromatography (TLC) (Silica gel, developed with ethyl acetate, Fisher) showed almost complete conversion. The newly formed precipitate was separated on a Buchner funnel and washed three times with hot dry benzene (800 mL total). The combined filtrates were evaporated to dryness on a rotary evaporator (Buchi, Fisher). The intermediate (II) was a white solid and used for the next step without further purification. An additional amount of the intermediate (II) was obtained from the solid retained by the Buchner funnel by resuspension in water and vacuum filtration. The combined collected solid was air dried. The overall yield of the crude intermediate (II) was virtually quantitative (110 g).

The crude II (2.9 g) was suspended in acetonitrile (25 mL, Fisher Chemicals). While the mixture was stirred at 50–60° C. with the pressure maintained through a balloon, trimethylamine (Aldrich) was introduced as the gas. After the conversion was complete, as indicated by TLC analysis, the mixture was vacuum filtered, washed repeatedly with acetonitrile and then air dried. The yield was 75% (2.5 g). LC-mass spectroscopy (Micromass, Beverly, Mass.) showed a major peak at Rf=9.8 min with mass of 454 daltons (M+H), as predicted. DHEA (8.75 g, 0.031 mol) was dissolved in benzene and triethylamine (4.45 mL) was added. 2-choro-1,3,2-dioxaphospholane-2-oxide (4.54 g, 0.032 mol, Aldrich) was then added at room temperature. The reaction mixture was stirred until complete conversion of DHEA to II occurred. The reaction was monitored by TLC (silica gel, ethyl acetate). After filtration, the solid was washed with dry benzene. The combined benzene solution was concentrated to give a white solid (II) and

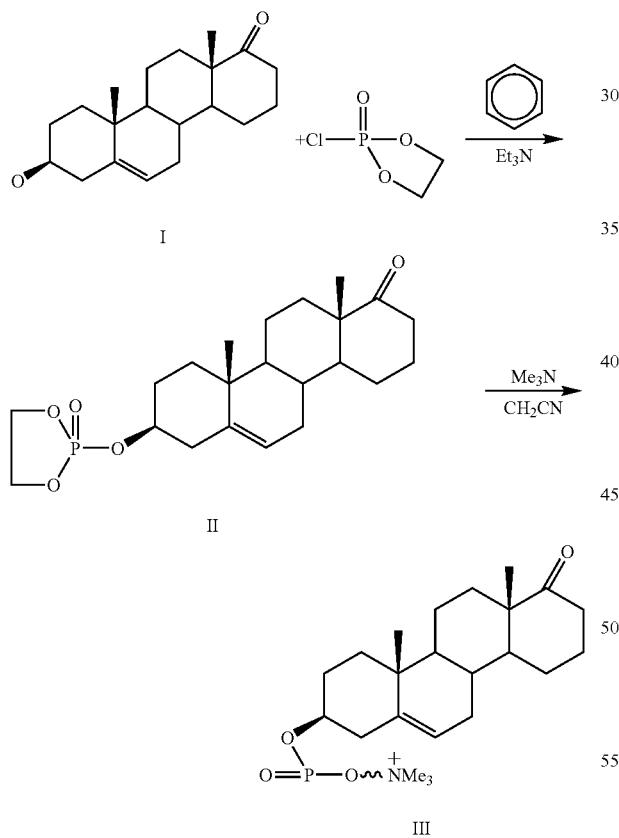

used without further purification.

A sample of II (0.75 g) pared as above was suspended in acetonitrile (10 mL) and stirred with heating. Trimethylamine was introduced as a gas while the pressure was regulated with a balloon attached to one of the necks of the flask. When TLC (silica gel, ethyl acetate) showed the disappearance of II, the addition of gas was stopped. The product (III) was collected by vacuum filtration, washed with additional acetonitrile and air dried. The yield was 0.72 g (83%).

The invention claimed is:

1. A compound having the general formula I:

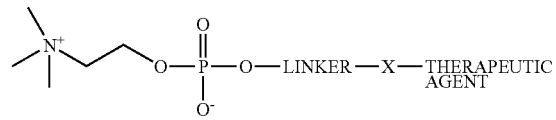

wherein the LINKER is one or more of the groups selected from the group consisting of (i) unsubstituted alkyl, (ii) substituted or unsubstituted alkenyl, (iii) unsubstituted alkanoyl, (iv) unsubstituted alkenoyl wherein the double bond is cis, and (v) (ortho or para) carbonyl-substituted aryl; and wherein the subtituent is each an independent group or linked together thereby forming a ring; and wherein X is an O or S atom and wherein the substituent is each an independent group or linked together thereby forming a ring; and wherein the therapeutic agent is selected from the group consisting of (i) testosterone, (ii) cardiotonic steroids selected from the group consisting of digitoxigenin, digoxigenin and ouabuquenin, (iii) dehydroepiandrosterone (DHEA), (iv) eticholanolone, (v) pregnenolone, (vi) estradiol, (vii) estrone, (viii) dexamethasone, (ix) hydrocortisone and (x) paclitaxel.

2. A compound according to claim 1, wherein the therapeutic agent is Propofol.

3. A compound according to claim 1, wherein said water-insoluble steroids are selected from the group consisting of (i) testosterone, (ii) cardiotonic steroids selected from the group consisting of digitoxigenin, digoxigenin and ouabugenin, (iii) dehydroepiandrosterone (DHEA), (iv) etiocholanolone, (v) pregnenolone, (vi) estradiol, (vii) estrone, (viii) dexamethasone and (ix) hydrocortisone.

4. A compound according to claim 1, further comprising one or more of the ingredients selected from the group consisting of pharmaceutically-acceptable carriers, diluents, fillers, salts, buffers, preservatives, antioxidants, a binder, an excipient, a disintegrating agent, a lubricant, and a sweetening agent.

5. A compound according to claim 1 incorporated into tablets, capsules or elixirs for oral administration; suppositories for rectal administration; sterile solutions or suspensions for injectable administration; or sterile solutions for ocular or internasal administration.

6. A compound having the general formula I:

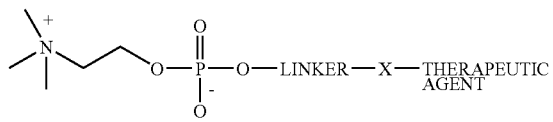

wherein the LINKER is a substituted alkanoyl of formula $CR_1R_2$—$CR_3R_4$—$CR_5R_6$—CO, wherein $R_1$, $R_2$, $R_3$, $R_4$, $R_5$, and $R_6$ are H, and wherein X is O and wherein the therapeutic agent is 2',6'-diisopropyl phenol.

7. The compound according to claim 1, wherein the therapeutic agent is paclitaxel is propofol.

8. The composition according to claim 2, further comprising a pharmaceutically-acceptable carrier selected from one or more binder, filter, salt, buffer, preservative, antioxidant, disintegrating agent, lubricant or sweetening agent.

9. The formulation of claim 8, wherein the physiologically acceptable carrier comprises one or more binder, preservative, stabilizer or flavor.

10. A compound having the general formula I:

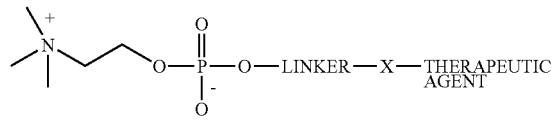

wherein the LINKER is a substituted alkenoyl of formula $CR_1R_2$—$CR_3$=$CR_4$—CO, wherein $R_1$, $R_2$, $R_3$, and $R_4$, are hydrogen, and wherein X is O and wherein the therapeutic agent is 2',6'-diisopropyl phenol.

11. A compound having the general formula I:

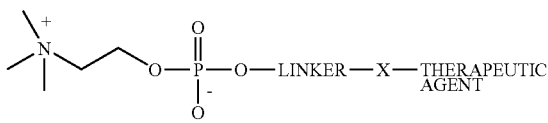

wherein the LINKER is of the formula aryl-ortho-$CR_3R_4$—$CR_5R_6$—CO, wherein $R_3$, $R_4$, $R_5$, and $R_6$, are hydrogen, and wherein X is O and wherein the therapeutic agent is 2',6'-diisopropyl phenol.

12. A compound having the general formula 1:

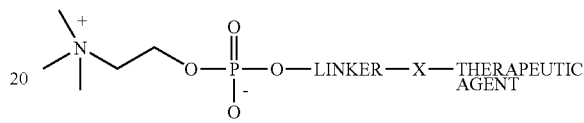

wherein the LINKER is a substituted alkenyl of formula $CR_1R_2$—$CR_3$=$CR_4$—CO, wherein $R_1$, $R_3$, and $R_4$, are hydrogen and wherein the double bond is trans, and wherein X is O and wherein the therapeutic agent is 2',6'-diisopropyl phenol.

* * * * *